United States Patent
Pacetti

(10) Patent No.: US 8,679,519 B2
(45) Date of Patent: Mar. 25, 2014

(54) COATING DESIGNS FOR THE TAILORED RELEASE OF DUAL DRUGS FROM POLYMERIC COATINGS

(75) Inventor: Stephen D. Pacetti, San Jose, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 1277 days.

(21) Appl. No.: 11/877,538

(22) Filed: Oct. 23, 2007

(65) Prior Publication Data

US 2009/0104247 A1   Apr. 23, 2009

(51) Int. Cl.
*A61F 2/00*   (2006.01)
*A61L 27/44*   (2006.01)

(52) U.S. Cl.
CPC .................................. *A61L 27/44* (2013.01)
USPC ....................................................... 424/424

(58) Field of Classification Search
None
See application file for complete search history.

(56) References Cited

U.S. PATENT DOCUMENTS

| | | | |
|---|---|---|---|
| 4,733,665 A | 3/1988 | Palmaz | |
| 4,800,882 A | 1/1989 | Gianturco | |
| 4,886,062 A | 12/1989 | Wiktor | |
| 5,464,650 A | 11/1995 | Berg et al. | |
| 6,746,773 B2 | 6/2004 | Llanos et al. | |
| 7,261,735 B2 | 8/2007 | Llanos et al. | |
| 7,591,844 B2 | 9/2009 | Llanos et al. | |
| 2005/0106204 A1 | 5/2005 | Hossainy et al. | |
| 2005/0158360 A1 | 7/2005 | Falotico et al. | |
| 2005/0169957 A1 | 8/2005 | Hossainy | |
| 2005/0208093 A1 | 9/2005 | Glauser et al. | |
| 2005/0287184 A1 | 12/2005 | Hossainy et al. | |
| 2006/0095120 A1 | 5/2006 | Herrmann | |
| 2006/0134168 A1 | 6/2006 | Chappa et al. | |
| 2006/0136048 A1* | 6/2006 | Pacetti et al. ................ 623/1.42 |
| 2006/0240070 A1 | 10/2006 | Cromack et al. | |
| 2007/0224240 A1 | 9/2007 | Toner et al. | |

FOREIGN PATENT DOCUMENTS

WO    WO 00/32238    6/2000
WO    WO 2007/146001    12/2007

OTHER PUBLICATIONS

International Search Report for PCT/US2008/080223 mailed Jan. 14, 2010, 16 pgs.

* cited by examiner

*Primary Examiner* — Bethany Barham
(74) *Attorney, Agent, or Firm* — Squire Sanders (US) LLP

(57) ABSTRACT

Provided herein are coating designs for the tailored release of two therapeutic agents from polymer coatings and methods of making and using the same.

12 Claims, 4 Drawing Sheets

COATING DESIGNS FOR THE TAILORED RELEASE OF DUAL DRUGS FROM POLYMERIC COATINGS

BACKGROUND OF THE INVENTION

1. Field of the Invention

The invention is generally related to coatings for implantable medical devices, such as drug delivery vascular stents for controlling the release rate of bioactive agents from the coating. This invention more particularly relates to coating designs for independently controlling the release of two bioactive agents from polymer coatings.

2. Description of the Related Art

Biomaterials research is continuously striving to improve the compositions from which medical articles, such as medical devices and coatings for medical devices, are produced. An example of a medical article is an implantable medical device.

A stent is an example of an implantable medical device that can benefit from improvements, such as a coating that can be used as a vehicle for delivering pharmaceutically active agents in a predictable manner. Stents can act as a mechanical intervention to physically hold open and, if desired, expand a passageway within a subject. Typically, a stent may be compressed, inserted into a small vessel through a catheter, and then expanded to a larger diameter once placed in a proper location. Examples of patents disclosing stents include U.S. Pat. Nos. 4,733,665, 4,800,882 and 4,886,062.

Stents play an important role in a variety of medical procedures such as, for example, percutaneous transluminal coronary angioplasty (PTCA), which is a procedure used to treat heart disease. In PTCA, a balloon catheter is inserted through a brachial or femoral artery, positioned across a coronary artery occlusion, inflated to compress atherosclerotic plaque and open the lumen of the coronary artery, deflated and withdrawn. Problems with PTCA include formation of intimal flaps or torn arterial linings, both of which can create another occlusion in the lumen of the coronary artery. Moreover, thrombosis and restenosis may occur several months after the procedure and create a need for additional angioplasty or a surgical by-pass operation. Stents are generally implanted to reduce occlusions, inhibit thrombosis and restenosis, and maintain patency within vascular lumens, such as the lumen of a coronary artery.

Stents are also being developed to provide local delivery of agents. Local delivery of agents is often preferred over systemic delivery of agents, particularly where high systemic doses are necessary to achieve an effect at a particular site within a subject—high systemic doses of agents can often create adverse effects within the subject. One method of local delivery includes coating the surface of a medical article with a polymeric carrier and attaching an agent to, or blending it with, the polymeric carrier.

Agent-coated stents have demonstrated dramatic reductions in the rates of stent restenosis by inhibiting the tissue growth associated with the restenosis. The process of restenosis in coronary artery disease is derived from an interplay of several implant-centered biological parameters. These are thought to be the combination of elastic recoil, vascular remodeling, and neointimal hyperplasia.

It has been found that the physiopathology of restenosis involves early injury to smooth muscle cells (SMCs), de-endothelialization and thrombus deposition. Inflammatory cells such as monocytes, neutrophils, and lymphocytes are recruited to the implant site in response to injury. Over time, this leads to SMC proliferation and migration and extracellular matrix deposition. There is an increasing body of evidence suggesting that inflammation plays a pivotal role in linking this early vascular injury with neointimal growth and eventual lumen compromise, i.e., restenosis. Further, it has been observed that, when stenting is used, the inflammatory state is often more intense and prolonged thus exacerbating the preceding effects.

Therefore, there is a need for developing a coating design for an implantable medical device that inhibits the growth of smooth muscle cells and endothelial cells, lowers the inflammation on healing, controls the release rates of bioactive agents and improves the mechanical properties.

The embodiments of the present invention address these concerns as well as others that are apparent to one having ordinary skill in the art.

SUMMARY OF THE INVENTION

Provided herein is a coating for an implantable medical device and the method of making and using the same. The coating comprises a first layer having a hydrophobic polymer and a olimus therapeutic agent; a second layer having a polar polymer and a non-olimus therapeutic agent; and a third optional primer layer, wherein the first layer is deposited over the second layer, wherein the second layer is deposited over the third layer, and wherein the coating provides independent control of the release of olimus and non-olimus therapeutic agents.

In certain embodiments, the coating further comprises an optional finishing coating layer for enhancing biocompatibility.

In some embodiments, the hydrophobic polymer in the coating is selected from a group consisting of poly(vinylidene fluoride), poly(vinylidene fluoride-co-chlorotrifluoroethylene), poly(vinylidene fluoride-co-hexafluoropropylene), poly(vinylidene chloride), poly(vinyl fluoride), poly(vinyl chloride), polyvinyl acetate, polystyrene, polyisobutylene, copolymers of styrene and isobutylene, poly(styrene-b-isobutylene-b-styrene), poly(n-butyl methacrylate), poly(butyl methacrylates), polycaprolactone, poly(trimethylene carbonate), poly(L-lactide), poly(L-lactic acid), poly(lactide-co-glycolide), poly(hydroxyvalerate), poly(3-hydroxyvalerate), poly(hydroxybutyrate), poly(3-hydroxybutyrate), poly(4-hydroxybutyrate), poly (hydroxybutyrate-co-valerate), poly(3-hydroxybutyrate-co-3-hydroxyvalerate), poly(glycolide), poly(glycolic acid), poly(D,L-lactide-co-L-lactide), poly(D,L-lactide-co-glycolide), poly(D,L-lactide), poly(D,L-lactic acid), poly(glycolic acid-co-trimethylene carbonate), polyanhydride, polyorthoester, SOLEF 21508 (formulation available from Solvay Solexis), acrylic polymers and acrylic copolymers, copolymers of vinyl monomers with each other and olefins, ethylene-methyl methacrylate copolymers, ethylene-vinyl acetate copolymers; ethylene-α-olefin copolymers, poly(silicone-urethanes), poly(tyrosine arylates), poly(tyrosine-derived carbonates); polyacrylates, polycarbonates, poly-hydroxycarboxylic acids, polyisobutylene and ethylene-α-olefin copolymers, polymethacrylates, polyolefins, polyorthoesters, polyvinyl aromatics; polyvinyl esters, silicones, vinyl copolymers, vinyl-olefin copolymers, vinyl halide polymers and copolymers.

In other embodiments, the polar polymer in the coating is selected from a group consisting of poly(ethylene-co-vinyl alcohol), EVAL, poly(vinyl alcohol), ethylene vinyl alcohol copolymers, poly(2-hydroxyethyl methacrylate), poly(2-hydroxyethyl methacrylate-co-n-butyl methacrylate), poly(2-hydroxyethyl methacrylate) copolymers, poly(2-methoxyethyl methacrylate), poly(2-ethoxyethyl methacrylate), poly(2-methoxy-1-methylethyl methacrylate), poly(carbamoylmethyl methacrylate), poly(2-carbamoylethyl methacrylate), poly(1-carbamoyl-1-methylmethyl methacrylate), poly(N-(carbamoylmethyl) methacrylamide), poly(N-(1-carbamoyl-1-methylmethyl)methacrylamide), poly(phosphorylcholine methacrylate), poly(phosphoryl choline methacrylate) copolymers, PC1036, PC2126, poly(cellulose ethers), poly(amino acids), poly(ester amides), poly(ester-urethanes), poly(ether-urethanes), poly(imino carbonates), poly(acrylic acids), poly(alkylene oxalates), polyamides, poly(carboxylic acids), polycyanoacrylates, polyethers, poly(imides), poly(ketones), poly(oxymethylenes), poly(phosphazenes), poly(phosphoesters), poly(phosphoester urethanes), poly(phosphoesters), polyurethanes, poly(vinyl esters), poly(vinyl ethers), poly(vinyl ketones), starch, sodium alginate, poly(vinyl pyrrolidone), poly(vinyl methyl ether), poly(isocyanate), poly(ethylene glycol), poly(dioxanone), poly(caprolactam), Nylon 66, hyaluronic acid, fibrinogen, fibrin, elastin-collagen, collagen, cellulose propionate, cellulose nitrate, cellulose butyrate, cellulose acetate butyrate, cellulose acetate, cellulose, carboxymethyl cellulose, chitin, chitosan, poly(N-acetylglucosamine), polyurethane, and PEO/PLA.

In some embodiments, the olimus therapeutic agent in the coating is selected from a group consisting of sirolimus (rapamycin), everolimus, zotarolimus, Biolimus A9, AP23572, tacrolimus, pimecrolimus and derivates or analogs or combinations thereof.

In certain embodiments, the non-olimus therapeutic agent in the coating is selected from a group consisting of dexamethasone, dexamethasone acetate, dexamethasone phosphate, dexamethasone valerate, dexamethasone derivatives, momentasone, clobetasol, cortisone, cortisone acetate, hydrocortisone, corticosterone, deoxycorticosterone, hydrocortisone acetate, deoxycorticosterone acetate, hydroxyprogesterone, prednisolone, prednisolone acetate, triamicinolone, triamicinolone acetonide, triamcinolone diacetate, betamethasone, betamethasone valerate, steroids, glucocorticoids, estradiol, methotrexate, azathioprine, vincristine, vinblastine, fluorouracil, doxorubicin hydrochloride, mitomycin, antiplatelet compounds, anticoagulants, antifibrin, antithrombins including sodium heparin, low molecular weight heparins, heparinoids, hirudin, argatroban, forskolin, vapiprost, prostacyclin, prostacyclin analogues, D-phe-pro-arg-chloromethylketone (synthetic antithrombin), dipyridamole, glycoprotein IIb/IIIa platelet membrane receptor antagonist antibody, recombinant hirudin, thrombin inhibitors including Angiomax ä, calcium channel blockers including nifedipine, colchicine, fibroblast growth factor (FGF) antagonists, histamine antagonists, lovastatin, monoclonal antibodies, nitroprusside, phosphodiesterase inhibitors, prostaglandin inhibitors, suramin, serotonin blockers, thioprotease inhibitors, triazolopyrimidine, nitric oxide or nitric oxide donors, super oxide dismutases, super oxide dismutase mimetic, cytostatic substances including angiopeptin, angiotensin converting enzyme inhibitors including captopril, cilazapril or lisinopril, antiallergic agents as in permirolast potassium, alpha-interferon, bioactive RGD and derivates or analogs or combinations thereof.

In other embodiments, the coating comprises a differentially permeable topcoat layer having a non-polar polymer; a drug reservoir layer having a polar polymer, a olimus therapeutic agent, a non-olimus therapeutic agent; and an optional primer layer, wherein the topcoat layer is deposited over the drug reservoir layer, wherein the drug reservoir layer is deposited over the primer layer, and wherein the permeable topcoat layer controls the release of olimus and non-olimus therapeutic agents.

In one embodiment, the polymer forming the differentially permeable topcoat layer in the coating is selected from a group consisting of poly(vinyl fluoride), poly(vinyl chloride), polystyrene, polyisobutylene, copolymers of styrene and isobutylene, poly(styrene-b-isobutylene-b-styrene), poly(n-butyl methacrylate), poly(butyl methacrylates), acrylic polymers, acrylic copolymers, copolymers of vinyl monomers with each other and olefins, ethylene-methyl methacrylate copolymers, ethylene-vinyl acetate copolymers; ethylene-α-olefin copolymers, poly(silicone-urethanes), poly(tyrosine arylates), poly(tyrosine-derived carbonates), polyacrylates, polycarbonates, polyisobutylene and ethylene-α-olefin copolymers, polymethacrylates, polyolefins, polyorthoesters, polyvinyl aromatics, polyvinyl esters, silicones, vinyl copolymers, vinyl-olefin copolymers, and vinyl halide polymers and copolymers.

In further embodiments, the coating comprises a first layer having a hydrophobic polymer and an olimus therapeutic agent; a second layer having a hydrophobic polymer and a crystallized non-olimus therapeutic agent; and a third, optional primer layer, wherein the first layer is deposited over the second layer, wherein the second layer is deposited over the third layer, and wherein the crystallized of non-olimus therapeutic agent has a slow rate of release from the coating so as to provide a control of release of the olimus and non-olimus therapeutic agents.

In another embodiment, the present invention describes a method, comprising implanting in a patient an implantable medical device comprising a coating as described herein, wherein the disorder is selected from the group consisting of atherosclerosis, thrombosis, restenosis, hemorrhage, vascular dissection or perforation, vascular aneurysm, vulnerable plaque, chronic total occlusion, patent foramen ovale, claudication, anastomotic proliferation for vein and artificial grafts, bile duct obstruction, ureter obstruction, tumor obstruction, and combinations thereof.

DETAILED DESCRIPTION OF THE INVENTION

Figure 1:
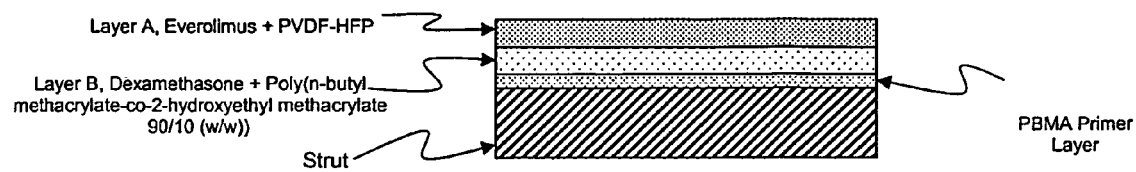
FIG. 1 illustrates a coating design for an implantable medical device according to some embodiments of the present invention.

As discussed in more detail below, the embodiments of the present invention generally encompass controlling release of two agents from an implantable medical device. More particularly, the present invention provides a coating on an implantable medical device which provides independent control of release of an olimus therapeutic agent and a non-olimus therapeutic agent from the coating.

Coating Designs

Provided herein is a method of independently modulating rate of release of at least two therapeutic agents from a coating by incorporating specific coating design and the method of making and using the coating.

As used herein, "hydrophobic" refers to a polymer that lacks an affinity for water. That is, it tends to repel water, to not dissolve in, mix with or be wetted by water or to do so only to a very limited degree and to not absorb water or, again, to do so only to a very limited degree. With regard to polymers, generally hydrophobicity increase with increasing alkyl content in the polymer backbone, that is, the greater the alkyl content in one or more of the constitutional units of the polymer. The hydrophobicity of a polymer may be characterized by determining the static contact angle of droplets of distilled water on a surface of the polymer. The greater the contact angle, the more hydrophobic the polymer. Generally speaking, a contact angle of greater than 90° indicates a hydrophobic polymer. The specifics or such measurements will not be presented here since they are well-known to those skilled in the art.

As used herein, "contact angle" is defined as an angle at the tangent of a droplet in a fluid phase that has taken an equilibrium shape on a solid surface under ambient condition.

As used herein, "hydrophobicity" can be gauged using the Hildebrand solubility parameter δ. The term "Hildebrand solubility parameter" refers to a parameter indicating the cohesive energy density of a substance. The δ parameter is determined as follows:

$$\delta = (\Delta E/V)^{1/2}$$

where δ is the solubility parameter, $(cal/cm^3)^{1/2}$;
ΔE is the energy of vaporization, cal/mole; and
V is the molar volume, $cm^3$/mole.

Accordingly, for the practice of the present invention, whether a material is hydrophobic or hydrophilic is relative. Between different materials, whichever has a lower Hildebrand value (δ) value compared to the δ value of the other is designated as a hydrophobic, and the material with a higher Hildebrand value (δ) value is designated as a hydrophilic. In one embodiment, the δ value defining the boundary between hydrophobic and hydrophilic can be between about 9.9 and 10.1 $(cal/cm^3)^{1/2}$. According to this embodiment, hydrophobic is defined as having a δ value equal to or below about 9.9 $(cal/cm^3)^{1/2}$, and hydrophilic is defined as having a δ value of about 10.1 $(cal/cm^3)^{1/2}$ or higher. Materials having a δ value between about 9.9 and 10.1 $(cal/cm^3)^{1/2}$ can exhibit behavior characterized by both hydrophilic and hydrophobic materials. Such materials are defined as "amphiphilic." Measurements other than Hildebrand value for the determination of hydrophobicity are known to those skilled in the art and may be employed in the same manner as the Hildebrand value to achieve the same end.

Representative examples of hydrophobic polymers include, but are not limited to, poly(vinylidene fluoride), poly(vinylidene fluoride-co-chlorotrifluoroethylene), poly(vinylidene fluoride-co-hexafluoropropylene), poly(vinylidene chloride), poly(vinyl fluoride), poly(vinyl chloride), polyvinyl acetate, polystyrene, polyisobutylene, copolymers of styrene and isobutylene, poly(styrene-b-isobutylene-b-styrene), poly(n-butyl methacrylate), poly(butyl methacrylates), polycaprolactone, poly(trimethylene carbonate), poly(L-lactide), poly(L-lactic acid), poly(lactide-co-glycolide), poly(hydroxyvalerate), poly(3-hydroxyvalerate), poly(hydroxybutyrate), poly(3-hydroxybutyrate), poly(4-hydroxybutyrate), poly(hydroxybutyrate-co-valerate), poly(3-hydroxybutyrate-co-3-hydroxyvalerate), poly(glycolide), poly(glycolic acid), poly(D,L-lactide-co-L-lactide), poly(D,L-lactide-co-glycolide), poly(D,L-lactide), poly(D,L-lactic acid), poly(glycolic acid-co-trimethylene carbonate), polyanhydride, polyorthoester, SOLEF 21508 (formulation available from Solvay Solexis), acrylic polymers and acrylic copolymers, copolymers of vinyl monomers with each other and olefins, ethylene-methyl methacrylate copolymers, ethylene-vinyl acetate copolymers; ethylene-α-olefin copolymers, poly(silicone-urethanes), poly(tyrosine arylates), poly(tyrosine-derived carbonates); polyacrylates, polycarbonates, poly-hydroxycarboxylic acids, polyisobutylene and ethylene-α-olefin copolymers, polymethacrylates, polyolefins, polyorthoesters, polyvinyl aromatics; polyvinyl esters, silicones, vinyl copolymers, vinyl-olefin copolymers, vinyl halide polymers and copolymers.

Representative examples of polar polymers include, but are not limited to, poly(ethylene-co-vinyl alcohol), EVAL, poly(vinyl alcohol), ethylene vinyl alcohol copolymers, poly(2-hydroxyethyl methacrylate), poly(2-hydroxyethyl methacrylate-co-n-butyl methacrylate), poly(2-hydroxyethyl methacrylate) copolymers, poly(2-methoxyethyl methacrylate), poly(2-ethoxyethyl methacrylate), poly(2-methoxy-1-methylethyl methacrylate), poly(carbamoylmethyl methacrylate), poly(2-carbamoylethyl methacrylate), poly(1-carbamoyl-1-methylmethyl methacrylate), poly(N-(carbamoylmethyl) methacrylamide), poly(N-(1-carbamoyl-1-methylmethyl)methacrylamide), poly(phosphorylcholine methacrylate), poly(phosphoryl choline methacrylate) copolymers, PC1036, PC2126, poly(cellulose ethers), poly(amino acids), poly(ester amides), poly(ester-urethanes), poly(ether-urethanes), poly(imino carbonates), poly(acrylic acids), poly(alkylene oxalates), polyamides, poly(carboxylic acids), polycyanoacrylates, polyethers, poly(imides), poly(ketones), poly(oxymethylenes), poly(phosphazenes), poly(phosphoesters), poly(phosphoester urethanes), poly(phosphoesters), polyurethanes, poly(vinyl esters), poly(vinyl ethers), poly(vinyl ketones), starch, sodium alginate, poly(vinyl pyrrolidone), poly(vinyl methyl ether), poly(isocyanate), poly(ethylene glycol), poly(dioxanone), poly(caprolactam), Nylon 66, hyaluronic acid, fibrinogen, fibrin, elastin-collagen, collagen, cellulose propionate, cellulose nitrate, cellulose butyrate, cellulose acetate butyrate, cellulose acetate, cellulose, carboxymethyl cellulose, chitin, chitosan, poly(N-acetylglucosamine), polyurethane, and PEO/PLA.

As used herein, "drug reservoir layer" refers either to a layer of one or more therapeutic agents applied neat or to a layer of polymer or blend of polymers that has dispersed within its three-dimensional structure one or more therapeutic agents. A polymeric drug reservoir layer is designed such that, by one mechanism or another, e.g., without limitation, by elution or as the result of biodegradation of the polymer, the therapeutic substance is released from the layer into the surrounding environment. For the purpose of this invention, the drug reservoir layer also acts as rate-controlling layer.

As used herein, a "primer layer" refers to a coating consisting of a polymer or blend of polymers that exhibit good adhesion characteristics with regard to the material of which the device body is manufactured and good adhesion characteristic with regard to whatever material is to be coated on the device body. Thus, a primer layer serves as an intermediary layer between a device body and materials to be affixed to the device body and is, therefore, applied directly to the device body. The presently preferred polymers for the primer layer include, but are not limited to, acrylate and methacrylate polymers, poly(n-butyl methacrylate), and copolymers thereof. Some additional examples of primers include, but are not limited to, poly(ethylene-co-vinyl alcohol), poly(vinyl acetate-co-vinyl alcohol), poly(methacrylates), poly(acrylates), polyethyleneamine, polyallylamine, chitosan, poly(ethylene-co-vinyl acetate), and parylene-C.

FIG. 1 illustrates a coating design for an implantable medical device according to some embodiments of the present invention. The coating comprises a first layer having a hydrophobic polymer and an olimus therapeutic agent. The presently preferred hydrophobic polymer is poly(vinylidene fluoride-co-hexafluoropropylene) (PVDF-HFP). The coating comprises a second layer having a polar polymer and a non-olimus therapeutic agent. The presently preferred polar polymer is poly(n-butylmethacrylate-co-2-hydroxyethylmethacrylate) (PBMA-co-HEMA) (90:10). The non-olimus therapeutic agent is dissolved in a polar polymer which prevents crystallization of non-olimus therapeutic agent. The coating comprises a third optional primer layer. The first layer is deposited over the second layer. The second layer is deposited over the third layer. The coating further comprises an optional finishing coating layer for enhancing biocompatibility. The specific coating design independently controls the release of olimus and non-olimus therapeutic agents.

As used herein, a "topcoat layer" refers to an outermost layer, that is, a layer that is in contact with the external environment and that is coated over all other layers. The topcoat layer may be a separate layer distinct from drug reservoir layer or the drug reservoir layer may itself be the outermost layer and therefore constitute the topcoat layer of a coating, if the drug reservoir layer contains hemocompatible and/or prohealing moieties. A separate topcoat layer may be applied to provide better hydrophilicity to the device, to better lubricate the device or merely as a physical protectant of the underlying layers.

Representative examples of the polymers of the differentially permeable topcoat layer include, but are not limited to, poly(vinyl fluoride), poly(vinyl chloride), polystyrene, polyisobutylene, copolymers of styrene and isobutylene, poly (styrene-b-isobutylene-b-styrene), poly(n-butyl methacrylate), poly(butyl methacrylates), acrylic polymers, acrylic copolymers, copolymers of vinyl monomers with each other and olefins, ethylene-methyl methacrylate copolymers, ethylene-vinyl acetate copolymers; ethylene-α-olefin copolymers, poly(silicone-urethanes), poly(tyrosine arylates), poly (tyrosine-derived carbonates), polyacrylates, polycarbonates, polyisobutylene and ethylene-α-olefin copolymers, polymethacrylates, polyolefins, polyorthoesters, polyvinyl aromatics, polyvinyl esters, silicones, vinyl copolymers, vinyl-olefin copolymers, and vinyl halide polymers and copolymers. In a presently preferred embodiment, the topcoat layer comprises styrene-isobutylene-styrene triblock polymer.

Figure 2:
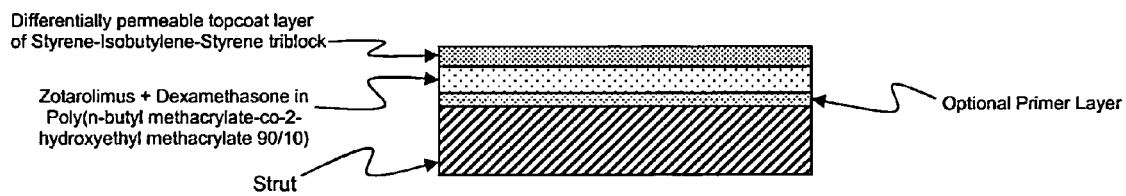
FIG. 2 illustrates a coating design for an implantable medical device according to some embodiments of the present invention.

FIG. 2 illustrates a coating design for an implantable medical device according to some embodiments of the present invention. The coating comprises a differentially permeable topcoat layer having a non-polar polymer; a drug reservoir layer having a polar polymer, an olimus therapeutic agent, a non-olimus therapeutic agent; and an optional primer layer. The topcoat layer is deposited over the drug reservoir layer. The drug reservoir layer is deposited over the primer layer. The coating further comprises an optional finishing coating layer for enhancing biocompatibility. Both the therapeutic agents are placed in a single drug reservoir layer. A different release rate for each therapeutic agent can be achieved by the use of a topcoat layer with differential permeability for each of the olimus therapeutic agent and the non-olimus therapeutic agent. The differentially permeable topcoat layer becomes functional for differentially controlling the rate of release of the agents when the permeability of the olimus and that of the non-olimus therapeutic agent differ at least by a factor of two. The drug permeability (P) is defined to be the product of the drug diffusivity (D) and the drug solubility (S) in the topcoat layer. The drug permeability (P), the drug diffusivity (D) and the drug solubility (S) are represented by the following equation:

$$P = D \times S$$

Generally, the non-olimus therapeutic agents are smaller molecules than the olimus therapeutic agent. Consequently, the diffusivity of the non-olimus therapeutic agent in the topcoat layer is higher than an olimus therapeutic agent. Normally, this higher diffusivity would mean that the non-olimus agent would always release more rapidly than the olimus agent. However, the solubility of the non-olimus therapeutic agent in the differentially permeable topcoat layer is lower than the olimus agent. This is because many of the non-olimus agents of interest are more polar than the olimus drugs. This leads to enhanced permeation of the olimus agent through the topcoat layer relative to the non-olimus agent. Therefore, the permeable topcoat layer controls the release of olimus and non-olimus therapeutic agents. The selective permeation of olimus therapeutic agent over non-olimus therapeutic agent can be achieved by using polymers such as silicone, poly(bl-styrene-bl-ethylene/butene-bl-styrene), silicone-urethanes and fluoro-silicones in the topcoat layer. The presently preferred differentially permeable polymer in the topcoat layer is styrene-isobutylene-styrene triblock polymer and the polymer in the drug reservoir layer is poly(n-butylmethacrylate-co-2-hydroxyethylmethacrylate) (PBMA-co-HEMA) (90:10). Polymers such as PVDF-HFP are not desired for this type of topcoat layer as they have enough polarity for the non-olimus therapeutic agent to have sufficient solubility to still be released much more rapidly than the olimus agent.

Figure 3:
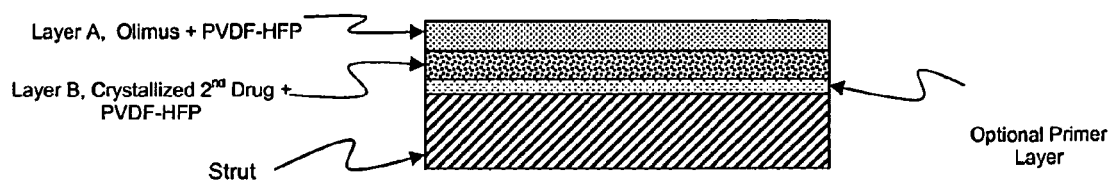
FIG. 3 illustrates a coating design for an implantable medical device according to some embodiments of the present invention.

FIG. 3 illustrates a coating design for an implantable medical device according to some embodiments of the present invention. The coating comprises a first layer having a hydrophobic polymer and an olimus therapeutic agent, which controls the release of an olimus therapeutic agent. The coating comprises a second layer having a hydrophobic polymer and a crystallized non-olimus therapeutic agent. The coating comprises a third optional primer layer. The first layer is deposited over the second layer. The second layer is deposited over the third layer. The coating further comprises an optional finishing coating layer for enhancing biocompatibility. The non-olimus therapeutic agent is crystallized in the hydrophobic polymer, poly(vinylidene fluoride-co-hexafluoropropylene) (PVDF-HFP), in the second layer. The second layer is saturated with crystallized non-olimus therapeutic agent dissolved in the layer. The dissolved non-olimus therapeutic agent can diffuse into the first layer only to the degree necessary to saturate the first layer which can be in very small amounts. The use of crystallization of the non-olimus therapeutic agent in a coating provides for control of the release rate of the non-olimus therapeutic agent. The presently preferred hydrophobic polymer for forming the first and second layer is poly(vinylidene fluoride-co-hexafluoropropylene) (PVDF-HFP). Overall, the coating shown in FIG. 3 provides control of release of both the olimus and non-olimus therapeutic agents.

Figure 4:
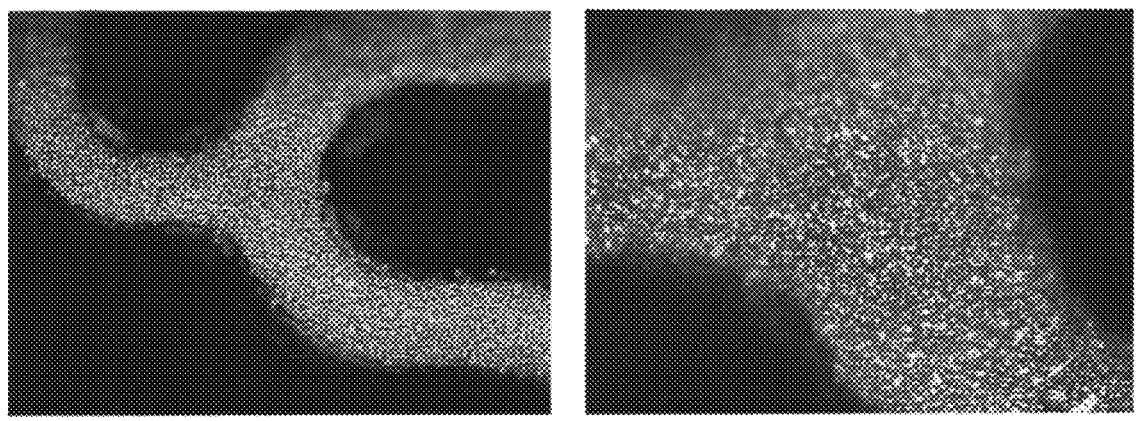
FIG. 4 illustrates an optical micrograph showing crystallization of a non-olimus therapeutic agent in the coating design for an implantable medical device according to some embodiments of the present invention.

FIG. 4 illustrates an optical micrograph showing crystallized non-olimus therapeutic agent in the coating for an implantable medical device according to some embodiments of the present invention shown in FIG. 3. The non-olimus therapeutic agent can be forced to crystallize out using hydrophobic polymer such as PVDF-HFP in the second layer. The process of crystallization of the non-olimus therapeutic agent in the second layer assures that the non-olimus therapeutic agent remains in the second layer. The crystal embolic hazard of the non-olimus therapeutic agent which can accompany the release of a crystal agent can be reduced as the crystals are buried in PVDF-HFP polymer in the second layer. As the second layer is saturated with crystallized non-olimus therapeutic agent, the variation in therapeutic agents release rate due to different degrees of crystallinity can be less when PVDF-HFP polymer in the second layer is saturated with dissolved non-olimus therapeutic agent and thus, the varying amount of crystals on the surface will not affect the release rate. Further, crystallization during aging is unlikely as the non-olimus therapeutic agent is insoluble in the PVDF-HFP that crystallization is likely to be complete after ETO sterilization. The non-olimus therapeutic agent in the second layer can be prevented from mixing into olimus therapeutic agent in the first layer by using a spray of volatile solvents such as acetone or 2-butanone.

Biocompatible Polymers

The coating described herein can include one or more biocompatible polymer. The biocompatible polymer can be biodegradable (either bioerodable or bioabsorbable) or non-degradable and can be hydrophilic or hydrophobic. The biocompatible polymer can be polar or non-polar in nature.

Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanoate) such as poly(4-hydroxybutyrate), poly(4-hydroxyvalerate), poly(4-hydroxyhexanoate), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly (ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly (isobutyl methacrylate), poly(tert-butyl methacrylate), poly (n-propyl methacrylate), poly(isopropyl methacrylate), poly (ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide/poly(lactic acid) (PEO/PLA)), polyalkylene oxides such as poly(ethylene oxide), poly(propylene oxide), poly (ether ester), polyalkylene oxalates, polyphosphazenes, phosphoryl choline, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), PLURONIC™ surfactants (polypropylene oxide-co-polyethylene glycol), poly(tetramethylene glycol), hydroxy functional poly(vinyl pyrrolidone), biomolecules such as chitosan, alginate, fibrin, fibrinogen, cellulose, starch, dextran, dextrin, fragments and derivatives of hyaluronic acid, heparin, fragments and derivatives of heparin, glycosamino glycan (GAG), GAG derivatives, polysaccharide, chitosan, alginate, or combinations thereof. In some embodiments, the copolymer described herein can exclude any one or more of the aforementioned polymers.

As used herein, the terms poly(D,L-lactide), poly(L-lactide), poly(D,L-lactide-co-glycolide), and poly(L-lactide-co-glycolide) can be used interchangeably with the terms poly (D,L-lactic acid), poly(L-lactic acid), poly(D,L-lactic acid-co-glycolic acid), or poly(L-lactic acid-co-glycolic acid), respectively.

Bioactive Agents

In embodiments, a coating described herein can optionally include one or more bioactive agents. These bioactive agents can be any agent which is a therapeutic, prophylactic, or diagnostic agent. These agents can have anti-proliferative or anti-inflammmatory properties or can have other properties such as antineoplastic, antiplatelet, anti-coagulant, anti-fibrin, antithrombonic, antimitotic, antibiotic, antiallergic, or antioxidant properties.

Presently preferred therapeutic agents of this invention are the olimus therapeutic agent and non-olimus therapeutic agent.

As used herein, "olimus" therapeutic agent refers to the family of therapeutic agents that include, but are not limited to, sirolimus (rapamycin), everolimus, zotarolimus, Biolimus A9 (Biosensors International, Singapore), AP23572 (Ariad Pharmaceuticals), tacrolimus, pimecrolimus and derivates or analogs or combinations thereof.

As used herein, a "non-olimus" therapeutic agent refers to a naturally occurring steroid hormone (corticosteroid) that is produced in the adrenal cortex and to synthetic therapeutic agents that exhibit corticosteroid-like pharmacological effects. Of particular importance to the methods of this invention is the ability of non-olimus therapeutic agent and their synthetic counterparts to mediate physiological systems related to the immune response and to regulation of inflammation.

Some examples of non-olimus therapeutic agents include, but are not limited to, dexamethasone, dexamethasone acetate, dexamethasone phosphate, dexamethasone valerate, dexamethasone derivatives, momentasone, clobetasol, cortisone, cortisone acetate, hydrocortisone, corticosterone, deoxycorticosterone, hydrocortisone acetate, deoxycorticosterone acetate, hydroxyprogesterone, prednisolone, prednisolone acetate, triamicinolone, triamicinolone acetonide, triamcinolone diacetate, betamethasone, betamethasone valerate, steroids, glucocorticoids, estradiol, methotrexate, azathioprine, vincristine, vinblastine, fluorouracil, doxorubicin hydrochloride, mitomycin, antiplatelet compounds, anticoagulants, antifibrin, antithrombins including sodium heparin, low molecular weight heparins, heparinoids, hirudin, argatroban, forskolin, vapiprost, prostacyclin, prostacyclin analogues, D-phe-pro-arg-chloromethylketone (synthetic antithrombin), dipyridamole, glycoprotein IIb/IIIa platelet membrane receptor antagonist antibody, recombinant hirudin, thrombin inhibitors including Angiomax, calcium channel blockers including nifedipine, colchicine, fibroblast growth factor (FGF) antagonists, histamine antagonists, lovastatin, monoclonal antibodies, nitroprusside, phosphodiesterase inhibitors, prostaglandin inhibitors, suramin, serotonin blockers, thioprotease inhibitors, triazolopyrimidine, nitric oxide or nitric oxide donors, super oxide dismutases, super oxide dismutase mimetic, cytostatic substances including angiopeptin, angiotensin converting enzyme inhibitors including captopril, cilazapril or lisinopril, antiallergic agents as in permirolast potassium, alpha-interferon, bioactive RGD and derivates or analogs or combinations thereof.

In addition to an olimus and a non-olimus therapeutic agent, an implantable medical device of this invention and the method herein may comprise additional therapeutic agents that are known or become known as being effective in treating the various physiological events comprising vascular diseases.

For example, other therapeutic agents that may be useful with the implantable medical device and method of this invention include, without limitation, antiproliferative agents, anti-inflammatory agents, antineoplastics and/or antimitotics, antiplatelet, anticoagulant, antifibrin, and antithrombin drugs, cytostatic or antiproliferative agents, antibiotics, antiallergic agents and antioxidants.

Antiproliferative agents include, without limitation, actinomycin D, taxol, docetaxel, paclitaxel and perfenidone.

Anti-inflammatory agents include, without limitation, alclofenac, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clopirac, cortodoxone, deflazacort, diclofenac potassium, diclofenac sodium, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid) and salicylic acid.

Anti-neoplastic and/or anti-mitotic agents include, without limitation, paclitaxel, docetaxel, methotrexate, azathioprine, vincristine, vinblastine, fluorouracil, doxorubicin hydrochloride, and mitomycin.

Antiplatelet, anticoagulant, antifibrin, and antithrombin agents include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä, calcium channel blockers such as nifedipine, colchicine, fish oil (omega 3-fatty acid), histamine antagonists, lovastatin, monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO) and estradiol.

Cytostatic or anti-proliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil ($\omega$-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide. Anti-allergenic agents include, without limitation, permirolast potassium.

Other potentially useful therapeutic agents include, without limitation, alpha-interferon, genetically engineered epithelial cells, DNA and RNA nucleic acid sequences, antisense molecules, and ribozymes, antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides, retroviral vectors; antiviral agents; analgesics; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers, beta-blockers such as pindolol, antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; natural or genetically engineered lipoproteins; and restenosis reducing agents.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by those of ordinary skill in the art.

Examples of Implantable Devices

As used herein, an implantable device can be any suitable medical substrate that can be implanted in a human or veterinary patient. Examples of such implantable devices include self-expandable stents, balloon-expandable stents, stent-grafts, grafts (e.g., aortic grafts), heart valve prosthesis (e.g., artificial heart valves) or vascular graft, cerebrospinal fluid shunts, pacemaker electrodes, catheters, endocardial leads (e.g., FINELINE and ENDOTAK, available from Guidant Corporation, Santa Clara, Calif.), and devices facilitating anastomosis such as anastomotic connectors. The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. The device can be, for example, a bioabsorbable stent.

Method of Use

In accordance with embodiments of the invention, a coating of the various described embodiments can be formed on an implantable device or prosthesis, e.g., a stent. For coatings including one or more active agents, the agent will be retained on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by atherosclerosis, abnormal or inappropriate migration and proliferation of smooth muscle cells, thrombosis, restenosis and the treatment of vulnerable plaque. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

The implantable device comprising a coating described herein can be used to treat an animal having a condition or disorder that requires a treatment. Such an animal can be treated by, for example, implanting a device described herein in the animal. Preferably, the animal is a human being. Exemplary disorders or conditions that can be treated by the method disclosed herein include, but not limited to, atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, and tumor obstruction.

EXAMPLES

The embodiments of the present invention will be illustrated by the following set forth examples. All parameters and data are not to be construed to limit the scope of the embodiments of the invention.

Example 1

Primer Layer: A solution (2%) of poly(n-butyl methacrylate) (PBMA) was formed by dissolving PBMA in acetone:cyclohexanone (70:30 by weight). An external air-assisted atomizing spray nozzle, such as an EFD 780S spray nozzle with a VALVEMATE 7040 control system (manufactured by EFD, Inc., East Providence, R.I.) was used for spraying the polymer solution onto the stent. The polymer solution was applied to stent while rotating in longitudinal axis at a speed of 150 rpm. The stent was moved linearly along the same axis at a speed of 6 mm/sec during the application. The PBMA polymer solution (2%) was applied to a 12-mm VISION™ stent (Abbott Vascular Inc.) in a series of 5-second passes to deposit 8 µg of coating per spray pass. The stent was dried for 10 seconds using a flow of air at ambient temperature between the spray passes. Eight spray passes were applied, followed by baking the primer layer at 80° C. for 30 minutes to form 60 µg a primer layer.

Second layer: A mixture of poly(n-butyl methacrylate-co-2-hydroxyethyl methacrylate) (PBMA-co-HEMA) (90:10) (2% by weight), dexamethasone (0.67%) and ethanol:n-butanol (50:50 by weight) (97.33%) was prepared. The mixture was applied to the stent by using the same apparatus as used for primer layer. Forty two spray passes were performed at 12 µg/pass to form a second layer, followed by drying at 50° C. for 1 hour to yield 480 µg of a second layer.

First layer: A mixture of poly(vinylidene fluoride-co-hexafluoropropylene) (PVDF-HFP) (85:15) (2%), everolimus (0.5%) and 2-butanone (97.5%). The mixture was applied to the stent by using the same apparatus as used for primer layer. Twenty five spray passes were performed at 12 μg/pass to form a first layer, followed by drying at 50° C. for 1 hour to yield 285 μg of a first layer.

Example 2

Primer Layer: A solution (2%) of poly(n-butyl methacrylate) (PBMA) was formed by dissolving PBMA in acetone:cyclohexanone (70:30 by weight). An external air-assisted atomizing spray nozzle, such as an EFD 780S spray nozzle with a VALVEMATE 7040 control system (manufactured by EFD, Inc., East Providence, R.I.) was used for spraying the polymer solution onto the stent. The polymer solution was applied to stent while rotating in longitudinal axis at a speed of 150 rpm. The stent was moved linearly along the same axis at a speed of 6 mm/sec during the application. The PBMA polymer solution (2%) was applied to a 12-mm VISION™ stent (Abbott Vascular Inc.) in a series of 5-second passes to deposit 8 μg of coating per spray pass. The stent was dried for 10 seconds using a flow of air at ambient temperature between the spray passes. Eight spray passes were applied, followed by baking the primer layer at 80° C. for 30 minutes to form 60 μg of a primer layer.

Drug reservoir layer: A mixture of poly(n-butyl methacrylate-co-2-hydroxyethyl methacrylate) (PBMA-co-HEMA) (90:10) (2% by weight), dexamethasone (0.67%), zotarolimus (0.5%) and ethanol:n-butanol (50:50 by weight) (96.83%) was prepared. The mixture was applied to the stent by using the same apparatus as used for primer layer. Eighteen spray passes were performed at 12 μg/pass to form a drug reservoir layer, followed by drying at 50° C. for 1 hour to yield 185 μg of a drug reservoir layer.

Topcoat layer: A mixture of poly(styrene-b-isobutylene-b-styrene) (25/50/25) (2% by weight), everolimus (0.5%) and tetrahydrofuran:toluene (50:50 by weight) (98%) was prepared. The mixture was applied to the stent by using the same apparatus as used for primer layer. Eighteen spray passes were performed at 12 μg/pass to form a topcoat layer, followed by drying at 50° C. for 1 hour to yield 200 μg of a topcoat layer.

Example 3

Primer Layer: A solution (2%) of poly(n-butyl methacrylate) (PBMA) was formed by dissolving PBMA in acetone:cyclohexanone (70:30 by weight). An external air-assisted atomizing spray nozzle, such as an EFD 780S spray nozzle with a VALVEMATE 7040 control system (manufactured by EFD, Inc., East Providence, R.I.) was used for spraying the polymer solution onto the stent. The polymer solution was applied to stent while rotating in longitudinal axis at a speed of 150 rpm. The stent was moved linearly along the same axis at a speed of 6 mm/sec during the application. The PBMA polymer solution (2%) was applied to a 12-mm VISION™ stent (Abbott Vascular Inc.) in a series of 5-second passes to deposit 8 μg of coating per spray pass. The stent was dried for 10 seconds using a flow of air at ambient temperature between the spray passes. Eight spray passes were applied, followed by baking the primer layer at 80° C. for 30 minutes to form 60 μg of a primer layer.

Second layer: A mixture of poly(vinylidene fluoride-co-hexafluoropropylene) (PVDF-HFP) (85:15) (2%), dexamethasone (2%) and acetone:cyclohexanone (70:30 by weight) (96%) was prepared. The mixture was applied to the stent by using the same apparatus as used for primer layer. Twenty one spray passes were performed at 12 μg/pass to form a second layer, followed by drying the second layer at 50° C. for 1 hour to yield 235 μg of a second layer.

First layer: A mixture of poly(vinylidene fluoride-co-hexafluoropropylene) (PVDF-HFP) (85:15) (2%), everolimus (0.5%) and 2-butanone (97.5%). The mixture was applied to the stent by using the same apparatus as used for primer layer. Twenty five spray passes were performed at 12 μg/pass to form a first layer, followed by drying at 50° C. for 1 hour to yield 285 μg of a first layer.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating for an implantable medical device, the coating comprising:
   a first layer comprising poly(vinylidene fluoride-co-hexafluoropropylene) and an olimus therapeutic agent;
   a second layer comprising a polar polymer and a non-olimus therapeutic agent;
   and a third optional primer layer deposited over a surface of the implantable medical device;
   wherein the first layer is deposited over the second layer;
   wherein the second layer is deposited over the third layer, if the third layer is present, or over a surface of the implantable medical device, if the third layer is not present;
   wherein the coating provides independent control of the release of the olimus and non-olimus therapeutic agents;
   wherein the polar polymer is selected from the group consisting of poly(ethylene-co-vinyl alcohol), poly(2-hydroxyethyl methacrylate-co-n-butyl methacrylate), and combinations thereof; and
   wherein the non-olimus therapeutic agent is selected from the group consisting of naturally occurring corticosteroids, synthetic therapeutic agents that exhibit corticosteroid-like pharmacological effects, and combinations thereof.

2. The coating of claim 1, wherein the implantable medical device is a stent.

3. The coating of claim 1, further comprising an optional finishing coating layer for enhancing biocompatibility.

4. The coating of claim 1, wherein the polar polymer in the second layer is poly(ethylene-co-vinyl alcohol).

5. The coating of claim 1, wherein the olimus therapeutic agent in the first layer is selected from the group consisting of sirolimus (rapamycin), everolimus, zotarolimus, Biolimus A9, AP23572, tacrolimus, pimecrolimus, and combinations thereof.

6. The coating of claim 1, wherein the non-olimus therapeutic agent in the second layer is selected from the group consisting of dexamethasone, dexamethasone acetate, dexamethasone phosphate, dexamethasone valerate, momentasone, clobetasol, cortisone, cortisone acetate, hydrocortisone, corticosterone, deoxycorticosterone, hydrocortisone acetate, deoxycorticosterone acetate, hydroxyprogesterone, prednisolone, prednisolone acetate, triamicinolone, triamicinolone acetonide, triamcinolone diacetate, betamethasone, betamethasone valerate, and combinations thereof.

7. The coating of claim 1, wherein the polar polymer in the second layer is poly(2-hydroxyethyl methacrylate-co-n-butyl methacrylate).

8. The coating of claim 1, wherein the olimus therapeutic agent in the first layer is everolimus.

9. The coating of claim 1, wherein the olimus therapeutic agent in the first layer is zotarolimus.

10. The coating of claim 1, wherein the non-olimus therapeutic agent in the second layer is selected from the group consisting of dexamethasone, dexamethasone acetate, dexamethasone phosphate, dexamethasone valerate, momentasone, clobetasol, and combinations thereof.

11. The coating of claim 1, wherein the olimus therapeutic agent in the first layer is everolimus, zotarolimus, or any combination thereof; and wherein the non-olimus therapeutic agent in the second layer is dexamethasone, dexamethasone acetate, dexamethasone phosphate, dexamethasone valerate, clobetasol, or any combination thereof.

12. The coating of claim 1, wherein the non-olimus therapeutic agent in the second layer is betamethasone, betamethasone valerate, or any combination thereof.

* * * * *

UNITED STATES PATENT AND TRADEMARK OFFICE
CERTIFICATE OF CORRECTION

PATENT NO. : 8,679,519 B2
APPLICATION NO. : 11/877538
DATED : March 25, 2014
INVENTOR(S) : Pacetti et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1513 days.

Signed and Sealed this
Eleventh Day of August, 2015

Michelle K. Lee
*Director of the United States Patent and Trademark Office*